US006336924B1

(12) United States Patent
Lecuyer et al.

(10) Patent No.: US 6,336,924 B1
(45) Date of Patent: Jan. 8, 2002

(54) EXTERNAL BIOLOGICAL FLUID DRAINAGE DEVICE

(75) Inventors: Alain Lecuyer, Grasse; Bernard Amann, Nice; Didier Rolland, Valbonne, all of (FR)

(73) Assignee: NMT Neurosciences Implants S.A., Sophia Antipolis (FR)

( * ) Notice: Subject to any disclaimer, the term of this patent is extended or adjusted under 35 U.S.C. 154(b) by 0 days.

(21) Appl. No.: 09/210,846

(22) Filed: Dec. 15, 1998

(30) Foreign Application Priority Data

Dec. 17, 1997 (FR) ........................................... 97 16020
Jul. 10, 1998 (FR) ........................................... 98 08871

(51) Int. Cl.[7] ................................................ A61M 1/00
(52) U.S. Cl. ....................................... 604/540; 604/327
(58) Field of Search ........................... 604/34, 118–119, 604/66, 250, 246–249, 540–544, 323, 317, 30–33, 327, 8

(56) References Cited

U.S. PATENT DOCUMENTS 3,799,702 A * 3/1974 Weishaar
4,631,061 A * 12/1986 Martin
4,661,093 A * 4/1987 Beck et al.
4,767,400 A * 8/1988 Miller et al.
4,798,583 A * 1/1989 Beck et al.
4,820,265 A * 4/1989 De Satnick et al.
5,624,394 A * 4/1997 Barnitz et al.
5,683,357 A * 11/1997 Magram

FOREIGN PATENT DOCUMENTS

DE 004111961 * 10/1992

* cited by examiner

*Primary Examiner*—Mark Bockelman
(74) *Attorney, Agent, or Firm*—Dennison, Scheiner, Schultz & Wakeman

(57) ABSTRACT

An external device for the drainage of biological fluid, particularly cephalorrhachidian fluid, utilizes a catheter (1, 2), one end of which is disposed in the area to be drained and the other end of which is connected to a drainage bag (3). This device includes a pressure measuring device (4) for measuring the pressure in the area to be drained and external flow control valve (5) on the catheter. An electronically controlled power supply (10) is provided for actuating the valve when the pressure exceeds a predetermined threshold.

9 Claims, 1 Drawing Sheet

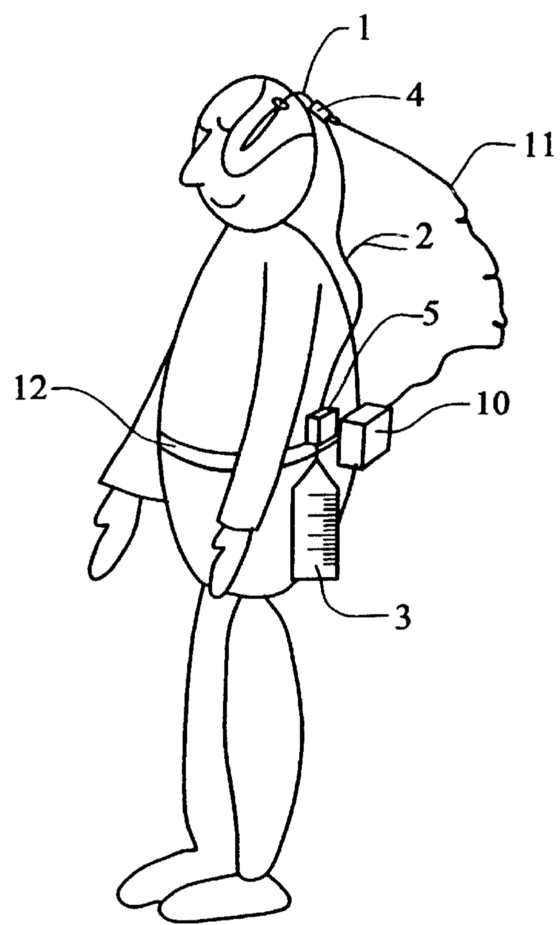
Fig. 1
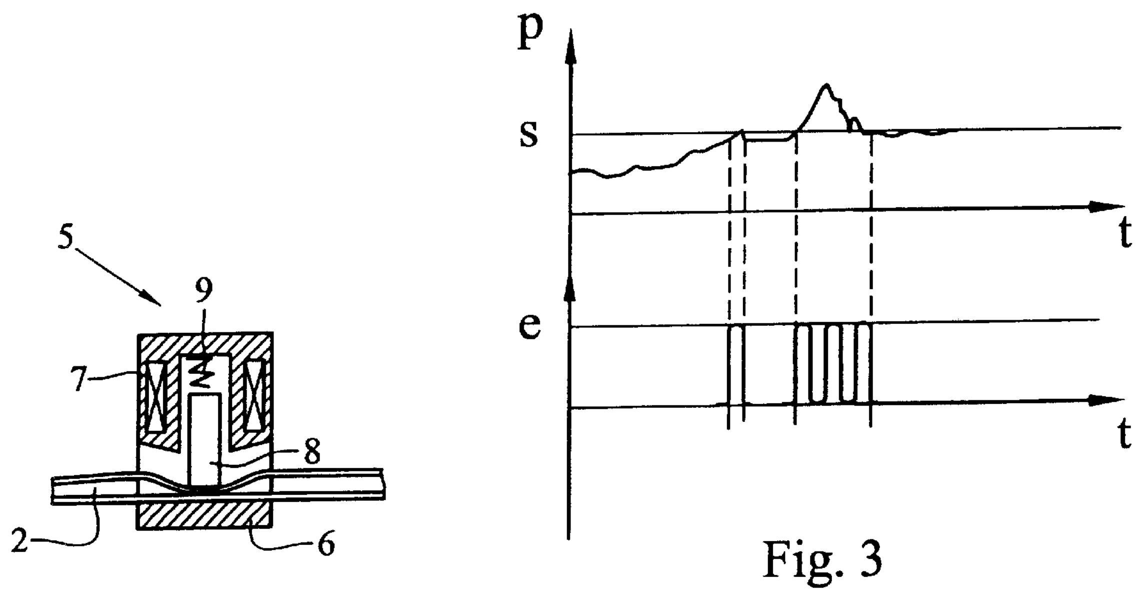
Fig. 2
Fig. 3

EXTERNAL BIOLOGICAL FLUID DRAINAGE DEVICE

BACKGROUND OF THE INVENTION

The present invention relates to an external device for the drainage of biological fluid, particularly cephalorrhachidian fluid.

The invention relates more particularly to ventricular drainage devices intended to regulate intracranial pressure. However, the drainage site could also be the lumbar space, the subarachnoid space, or any other site that allows drainage, particularly of cephalorrhachidian fluid.

There are already several known types of implantable valves intended for controlling the drainage of excess cephalorrhachidian fluid contained in the cerebral ventricles, for example the peritoneal cavity. These valves are generally intended for the treatment of hydrocephalus.

Thus, the use of simple pressure regulating valves is known. The drawback of these valves is that they do not take into account the differences in the water level that result from of the position of the patient, particularly when lying down or standing.

It has also been proposed to use needle and diaphragm valves having a so-called "anti-siphon" feature, thus avoiding the above drawback. Although often satisfactory, they are intended to be implanted, and therefore are not suitable for short-term use, for example following a trauma.

The known external drainage systems are constituted by a simple catheter, one end of which is disposed in the area to be drained, and the other end of which is connected to a drainage bag. Since they have no pressure regulating means having an "anti-siphon" type feature, they do not allow the patient to stand. Moreover, their settings need to be checked after the patient is moved (washing, transporting, etc.).

The simple addition of a pressure regulator does not constitute a suitable solution. These regulators are in fact relatively complicated devices subject to obstructions if the cephalorrhachidian fluid is mixed with blood. Moreover, their cost is high.

SUMMARY OF THE INVENTION

The object of the present invention is to overcome the disadvantages of the prior art devices.

To this end, the subject of the invention is an external device for the drainage of biological fluid, particularly cephalorrhachidian fluid, comprising a catheter, one end of which is disposed in the area to be drained and the other end of which is connected to a drainage bag, characterized in that it comprises pressure measuring means for measuring the pressure in the area to be drained, and external flow control means controlling flow through the catheter, an electronically controlled power supply being provided for actuating the flow control means when the pressure exceeds a predetermined threshold.

Thus, the pressure in the area to be drained is regulated directly and simply. The flow control means and their power supply are outside the cephalorrhachidian fluid circuit and are therefore reusable. Only the catheter, the drainage bag, and possibly the pressure measurement means if the fluid to be drained has direct contact with them, are disposable.

In the case of external ventricular drainage, a device of this type is not sensitive to the position of the patient, who can stand up and move, or be moved, without any adjustment of the system.

Various types of flow control means can be used.

In a first case, this could be progressive means such as a pump or a valve operated by a motor.

In another case, this could be a means that operate in an all-or-nothing mode such as a pinch valve or flap valve.

In the latter case, the valve is normally closed and opens when the pressure threshold is reached. This opening can occur in pulses, the pulses continuing until the pressure has fallen back below the threshold.

In one particular embodiment, the pressure measuring means is disposed on a drainage line. More particularly, the means can be disposed between one catheter part, one end of which is inserted into the ventricle to be drained, and another catheter part connected to the drainage bag.

However, in another embodiment, it is possible to use an independent implantable catheter comprising a sensor in its distal part. In the case of ventricular drainage, it is possible to use any other means for measuring intracranial pressure that issues a signal compatible with the electronic control of the power supply.

In another particular embodiment, the electronic control is disposed to read the pressure at predetermined time intervals, and if the pressure is higher than the threshold, to activate said flow control means for a duration that is also predetermined.

BRIEF DESCRIPTION OF THE DRAWINGS

As a non-limiting example, a particular embodiment of the invention will now be described in reference to the appended schematic drawings, in which:

FIG. 1 represents the various elements of a device according to the invention for external ventricular drainage, as fitted onto a patient;

FIG. 2 is an enlarged, cross-sectional view of the valve shown in FIG. 1; and FIG. 3 is a graph of the pressure measurement signal and the control signal over a period of time.

DESCRIPTION OF THE PREFERRED EMBODIMENTS

The device according to the invention comprises a drainage catheter in two parts, a first part 1 in the vicinity of the patient's head and a second part 2 in the vicinity of a drainage bag 3. A pressure sensor 4 of any known type is disposed between the parts 1 and 2 of the catheter. This sensor is disposed in immediate proximity to the patient's head in order to measure the intracranial pressure independently of the position of the patient.

One of the ends of the part 1 of the catheter is inserted in a known way into a ventricle of the patient's brain to be drained. Its other end is connected to the input of the pressure sensor 4.

The output of the sensor 4 is connected to one end of the part 2 of the drainage catheter. The other end of this part 2 is connected to a drainage bag 3. This drainage line could also be embodied in several parts.

The bag 3 is made of transparent plastic material and is graduated to make it possible to measure the quantity of fluid drained. It can also be equipped with a drop counting system, for example an optical one.

A pinch valve 5 shown in FIG. 2 is disposed on the part 2 of the drainage catheter. This valve is composed of a body 6 forming a clamp into which the catheter is inserted in order to be closed by pinching.

One of the branches of the valve body 6 receives an electromagnet whose coil 7 is supplied with power as described below. The core 8 of the electromagnet forms a plunger capable of pressing the catheter 2 against the other branch of the valve body 6. A compression spring 9 is disposed between the body 6 and the core 8 for pushing the core in the direction of the catheter 2 and pinch it.

An electronic power pack 10 receives from the sensor 4 through a wire 11 an electrical signal representing the pressure p measured and compares it to a threshold value s in order to control the opening of the valve when the pressure exceeds this threshold. In addition, the pack 10 provides the electric power supply for the sensor 4.

FIG. 3 shows an example of the evolution over time of the measured intracranial pressure p and the resulting control voltage e to the electromagnet.

In the absence of power supplied to the electromagnet, the valve 5 is normally closed. When the pressure p exceeds the threshold s, the electronics of the pack 10 are disposed to send voltage pulses into the coil 7 so as to retract the core 8 against the action of the spring 9, thus opening the valve. Fluid flows out and the pressure decreases. When it becomes lower than the threshold, the valve ceases to be activated.

It will be noted that it is possible to perform a smoothing of the signal issued by the sensor 4.

It is also possible to read the pressure only at predetermined time intervals, for example every 10 seconds, and if the pressure is higher than the threshold, to hold the valve open for a duration that is also predetermined, for example one second. It is also possible to obtain a limitation of the flow.

Lastly, the device is advantageously supplemented by a belt 12 to which the power pack 10 and the drainage bag 3 can be attached. Thus, the patient is perfectly mobile.

It is understood that the pack could also be attached to the patient's bed or to a support near the bed.

The electronics described have been reduced to their simplest expression. But it would also be possible to provide a means for connecting to a recording device or a microcomputer in order to record, among other things, the evolution of the pressure as a function of time, and simultaneously analyze it. In a variant, storage means could be provided in the electronic pack, in which case the recordings could be analyzed a posteriori on a microcomputer.

It is also possible to use pressure measuring means connected to a general monitoring center of a hospital, particularly one that is equipped to generate alarms if necessary. In this case, the pinch valve, or any other regulating device, could be controlled remotely from this monitoring center.

The pack itself could comprise alarms and/or displays.

What is claimed is:

1. An external device for the drainage of cerebro-spinal fluid from a body of a patient in need thereof, comprising:

a catheter having a first end arranged to be disposed in the area to be drained and a second end connected to a drainage bag;

means for measuring fluid pressure in the area to be drained;

external flow control means for controlling fluid flow through said catheter to said drainage bag;

an electronically controlled power supply constructed and arranged to read the pressure measured by the means for measuring fluid pressure at predetermined time intervals and for actuating said flow control means when the pressure exceeds a predetermined threshold, to permit fluid flow through the catheter to the drainage bag for a predetermined duration; and external fastening means for fixing at least the power supply and the drainage bag onto the body of the patient.

2. The device according to claim 1, in which said flow control means is progressive means.

3. The device according to claim 1, in which said flow control means comprises a pinch valve.

4. The device according to claim 3, in which the catheter comprises a tube which passes through the pinch valve.

5. The device according to claim 4, wherein the pinch valve is a normally closed valve comprising means for applying pressure to the catheter and means for releasing the pressure applied to the catheter when actuated by the electronically controlled power supply.

6. The device according to claim 1, in which said pressure measuring means comprises an independent implantable catheter comprising a sensor in its distal part.

7. The device according to claim 1, in which said pressure measuring means is disposed in a drainage line comprising the catheter.

8. The device according to claim 7, in which said pressure measuring means is disposed between the first catheter end inserted into the area to be drained, and the second catheter end connected to the drainage bag.

9. The device according to claim 1, wherein the means for measuring fluid pressure comprises a pressure sensor disposed in immediate proximity to said first end of the catheter.

* * * * *